(12) United States Patent
Jonsson et al.

(10) Patent No.: US 11,529,264 B2
(45) Date of Patent: Dec. 20, 2022

(54) TAMPON APPLICATOR

(71) Applicant: Essity Hygiene and Health Aktiebolag, Gothenburg (SE)

(72) Inventors: Sylvia Jonsson, Gothenburg (SE); Conny Dahlqvist, Gothenburg (SE); Susanne Carlstedt, Malmö (SE); Malkus Arlemark, Malmö (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/652,240

(22) PCT Filed: Oct. 6, 2017

(86) PCT No.: PCT/EP2017/075542
§ 371 (c)(1),
(2) Date: Mar. 30, 2020

(87) PCT Pub. No.: WO2019/068350
PCT Pub. Date: Apr. 11, 2019

(65) Prior Publication Data
US 2020/0246196 A1     Aug. 6, 2020

(51) Int. Cl.
*A61F 13/26* (2006.01)
*A61F 13/20* (2006.01)

(52) U.S. Cl.
CPC .......... *A61F 13/26* (2013.01); *A61F 13/2022* (2013.01)

(58) Field of Classification Search
CPC .... A61F 13/26; A61F 13/266; A61F 13/2022; A61F 13/2037; A61F 6/18; A61F 13/263
See application file for complete search history.

(56) References Cited

U.S. PATENT DOCUMENTS

| | | | |
|---|---|---|---|
| 3,645,263 A | 2/1972 | Bates | |
| 3,696,812 A | 10/1972 | Jaycox | |
| 3,765,416 A * | 10/1973 | Werner | A61F 13/26 604/18 |
| 3,835,856 A | 9/1974 | Warncke | |
| 4,361,150 A | 11/1982 | Voss | |
| 4,479,791 A * | 10/1984 | Sprague | A61F 13/263 604/14 |
| 4,676,773 A | 6/1987 | Sheldon | |

(Continued)

FOREIGN PATENT DOCUMENTS

| AU | 2012218945 A1 | 8/2013 |
|---|---|---|
| CA | 945703 A | 4/1974 |

(Continued)

OTHER PUBLICATIONS

Dictionary.com definition of "at", May 12, 2022.*

(Continued)

*Primary Examiner* — Catharine L Anderson
(74) *Attorney, Agent, or Firm* — Cantor Colburn LLP (57) ABSTRACT

An applicator for a tampon is provided. The applicator has an inner tube and an outer tube and the inner tube is slideable within the outer tube. The applicator has a forward end, and the inner surface of the outer tube has an annular protrusion near to the rear end of the outer tube. The internal diameter of the outer tube is smaller rearward of the annular protrusion than forward of the annular protrusion.

10 Claims, 6 Drawing Sheets

(56) References Cited

U.S. PATENT DOCUMENTS

| | | | |
|---|---|---|---|
| 4,891,042 | A | 1/1990 | Melvin et al. |
| 4,960,417 | A | 10/1990 | Tarr et al. |
| 5,080,659 | A | 1/1992 | Nakanishi |
| 5,554,109 | A | 9/1996 | Frayman |
| 5,569,177 | A | 10/1996 | Fox et al. |
| 5,571,540 | A | 11/1996 | Weyenberg et al. |
| 5,817,047 | A | 10/1998 | Osborn, III et al. |
| 6,019,744 | A | 2/2000 | Altdorf et al. |
| 6,432,076 | B1 | 8/2002 | Wada et al. |
| 8,777,916 | B2 * | 7/2014 | Van Ingelgem ...... A61F 13/263 604/16 |
| D726,313 | S * | 4/2015 | Govers .......... D24/141 |
| 10,918,515 | B2 * | 2/2021 | Callaghan ............ A61F 13/28 |
| 2003/0028138 | A1 | 2/2003 | Karapasha et al. |
| 2003/0144639 | A1 | 7/2003 | Gehling |
| 2005/0273043 | A1 | 12/2005 | Osborn et al. |
| 2007/0021708 | A1 | 1/2007 | Bertulis et al. |
| 2008/0154176 | A1 * | 6/2008 | Van Ingelgem ........ A61F 13/26 604/11 |
| 2008/0195029 | A1 * | 8/2008 | Van Ingelem ...... A61F 13/2034 604/14 |
| 2008/0243046 | A1 | 10/2008 | Cettina et al. |
| 2009/0192436 | A1 | 7/2009 | Karapasha et al. |
| 2010/0016780 | A1 * | 1/2010 | VanDenBogart ....... A61F 13/26 604/15 |
| 2010/0324468 | A1 * | 12/2010 | Gann .................... A61F 13/266 604/15 |
| 2011/0201992 | A1 | 8/2011 | Smet et al. |
| 2011/0273727 | A1 * | 11/2011 | Seki ..................... A61F 13/266 356/634 |
| 2014/0052048 | A1 | 2/2014 | Taniguchi et al. |
| 2014/0155809 | A1 | 6/2014 | Taniguchi et al. |
| 2016/0296380 | A1 | 10/2016 | Graham et al. |
| 2017/0246042 | A1 | 8/2017 | Ferrer et al. |

FOREIGN PATENT DOCUMENTS

| | | | |
|---|---|---|---|
| CN | 1229351 | A | 9/1999 |
| CN | 101155568 | A | 4/2008 |
| CN | 101346114 | A | 1/2009 |
| CN | 102088942 | A | 6/2011 |
| CN | 102341080 | A | 2/2012 |
| CN | 103384508 | A | 11/2013 |
| CN | 206007475 | U | 3/2017 |
| CO | 00019628 | | 3/2000 |
| EP | 1695680 | A1 | 8/2006 |
| EP | 1704841 | A1 | 9/2006 |
| EP | 2404585 | A1 | 1/2012 |
| EP | 2737887 | A1 | 6/2014 |
| GB | 2220359 | A | 1/1990 |
| JP | 2012183305 | A | 9/2012 |
| JP | 2013111180 | A * | 6/2013 ............. A61F 13/26 |
| KR | 20090031013 | A | 3/2009 |
| RU | 2406473 | C2 | 12/2010 |
| WO | 9011747 | A1 | 10/1990 |
| WO | 2007115091 | A1 | 10/2007 |
| WO | 2010046478 | A1 | 4/2010 |
| WO | 2012111342 | A1 | 8/2012 |
| WO | WO-2016156403 | A1 * | 10/2016 ........... A61K 9/0036 |

OTHER PUBLICATIONS

International Preliminary Report on Patentability for International Application No. PCT/EP2017/075542, dated Aug. 19, 2019, 11 pages.
International Search Report and Written Opinion for International Application PCT/EP2017/075542, dated Feb. 14, 2018, 9 pages.
International Preliminary Report on Patentability for International Application No. PCT/EP2017/075539, dated Sep. 16, 2019, 12 pages.
International Search Report and Written Opinion for International Application PCTEP2017/075539, dated Jan. 25, 2018, 11 pages.
International Search Report and Written Opinion for International Application No. PCT/EP2017/075541, dated Feb. 12, 2018, 8 pages.
International Preliminary Report on Patentability for International Application No. PCT/EP2017/075543, dated Sep. 18, 2019, 13 pages.
International Search Report and Written Opinion for International Application PCT/EP2017/075543, dated Feb. 14, 2018, 8 pages.
China National Intellectual Property Administration, Office Action, Application No. 201780094581.1, dated Aug. 10, 2020 (8 pages).
China National Intellectual Property Administration, Office Action, Application No. 201780094573.7, dated Aug. 7, 2020 (10 pages).
China National Intellectual Property Administration, Office Action, Application No. 201780094572.2, dated Aug. 7, 2020 (11 pages).
Federal Service for Intellectual Property, Decision To Grant, Russian Application No. 2020115156, dated Aug. 27, 2020 (17 pages).
Federal Service for Intellectual Property, Decision To Grant, Russian Application No. 2020115119, dated Aug. 14, 2020 (18 pages).
Federal Service for Intellectual Property, Decision To Grant, Russian Application No. 2020115036, dated Aug. 14, 2020 (18 pages).
China National Intellectual Property Administration, Second Office Action, Application No. 201780094581.1, dated Apr. 8, 2021 (22 pages).
European Patent Office, Communication pursuant to Article 94(3) EPC, Application No. 17780737.7-1102, dated Apr. 30, 2021 (3 pages).
Colombian Patent Office, Office Action 18766, Application No. NC2020/0004361, dated Nov. 29, 2021 (6 pages).

* cited by examiner

Fig. 5
Detail E

Fig. 6
Section B-B

Fig. 10
Section C-C

TAMPON APPLICATOR

CROSS REFERENCE TO RELATED APPLICATIONS

This is a U.S. National Phase application of PCT/EP2017/075542, filed Oct. 6, 2017, the disclosure of which is incorporated herein by reference in its entirety for all purposes.

TECHNICAL FIELD

The present disclosure relates to tampon applicators.

BACKGROUND

Tampons are female hygiene absorbent products used to absorb menstrual blood flow within the body of a user. Tampons may be provided with or without applicators. When no applicator is provided, the tampon is generally inserted manually by the user. However many women prefer to use an applicator to facilitate insertion of the tampon and/or for hygiene reasons.

Known tampon applicators generally include two cylindrical tubes arranged in a telescopic relationship with each other, one tube being slideable within the other tube. In one arrangement, the tampon is provided within the outer tube whilst the inner tube is provided within the outer tube behind the tampon and extending outside of the outer tube in a rearward direction. In use, the user inserts the outer tube into the body and pushes the rearwardly extending portion of the inner tube in a forward direction towards the tampon, and the front part of the inner tube makes contact with and pushes the tampon out of the outer tube and into the body of the user. It will be appreciated that, as the inner tube is only partially inserted into the outer tube, such applicators are relatively bulky.

In another arrangement, where the applicators may be referred to as "compact" or "collapsible" applicators, the tampon is located in the inner tube and the inner tube is almost entirely contained within the outer tube. This provides a more compact and discreet applicator. In such applicators, in use, the user first pulls an exposed rear part of the inner tube in a rearward direction so that the inner tube slides rearwardly with respect to the outer tube, thereby exposing most of the inner tube. Whilst the inner tube is being slid relative to the outer tube, the front end of the tampon may be engaged by the outer tube to help to hold the tampon in place whilst the inner tube is being rearwardly extended. In this manner, the tampon stays in position with respect to the outer tube whilst the inner tube slides backwards and extends rearwardly of the outer tube. This movement of the inner tube relative to the tampon and the outer tube results in the inner tube sliding in a rearward direction over the tampon and leaving the tampon within the outer tube. Once the tampon is no longer held within the inner tube and the inner tube is positioned rearwardly of the tampon, the outer tube may be inserted into the body of the user and the rearwardly extending portion of the inner tube may be pushed in a forward direction towards the tampon. The front part of the inner tube ideally then makes contact with the tampon and pushes the tampon out of the outer tube and into the body of the user.

It would be desirable to provide an applicator that is of the compact type and which permits a user to more accurately, easily and comfortably insert a tampon into the body.

SUMMARY

According to the present disclosure there is provided an applicator for a tampon comprising an inner tube and an outer tube, the inner tube being slideable within the outer tube, the applicator having a forward end, wherein the inner surface of the outer tube comprises an annular protrusion near to the rear end of the outer tube and the internal diameter of the outer tube is smaller rearward of the annular protrusion than forward of the annular protrusion.

The applicator may be of a compact type. The inner tube of the applicator may be configured to receive a tampon. The forward end refers to the front or distal end of the applicator, i.e. the part of the applicator which is inserted into the body. The rear or rearward end refers to the back or proximal end of the applicator, i.e. the part of the applicator which is not inserted into the body and which is handled by the user.

When a user inserts a tampon using an applicator, it is desirable that a minimum amount of force is required to eject the tampon from the outer tube. This is because the user does not want to cause herself discomfort or pain if the tampon is not properly aligned with the vaginal cavity and is suddenly and forcefully ejected. New users of tampons, in particular, may find it difficult to correctly align and insert a tampon and are likely to be more cautious and to push out the tampon from the outer tube quite slowly.

If the inner tube and the outer tube are not in close alignment with each other along the longitudinal direction of the applicator whilst the inner tube is being pushed forwards to eject the tampon, the force required to eject the tampon increases. The greater the angle between the longitudinal axis of the inner tube and the longitudinal axis of the outer tube, the harder it becomes to push the tampon out of the inner tube. This is because the front end of the inner tube makes contact with the inner surface of the outer tube, thereby increasing the resistance to movement of the inner tube with respect to the outer tube.

By providing that the rearward part of the outer tube has a smaller internal diameter than the main or central part of the outer tube, the inner tube may be guided by the rearward part of the outer tube to move forwards in a direction along or at least closely aligned with the longitudinal axis of the outer tube, thereby reducing the force required to push the tampon out of the outer tube and improving the alignment of the tampon with the vaginal cavity. This makes the process of inserting a tampon easier and more comfortable for the user.

The annular protrusion may be configured to engage with one or more protrusions on the outer surface of the inner tube at or near the forward end of the inner tube, to thereby prevent the inner tube from being slid completely out of the rear end of the outer tube.

The internal diameter of the outer tube rearward of the annular protrusion may be greater than the internal diameter of the outer tube at the region of the annular protrusion. Alternatively the internal diameter of the outer tube rearward of the annular protrusion may be the same or similar to the internal diameter of the outer tube at the region of the annular protrusion. In this case the annular protrusion may take the form of a step extending around the interior of the outer tube in a circumferential direction.

The internal diameter of the outer tube rearward of the annular protrusion may be substantially constant along the longitudinal length of the outer tube from the annular protrusion to the rear end of the outer tube. Alternatively the internal diameter of the outer tube rearward of the annular protrusion may be tapered along the longitudinal length of the outer tube from the annular protrusion to the rear end of the outer tube, the internal diameter of the outer tube rearward of the annular protrusion being smaller throughout the taper than the internal diameter of the outer tube forward of the annular protrusion.

The external diameter of the outer tube may be tapered at its rearward end such that the external diameter of the outer tube increases towards the rear end of the outer tube. This may assist users in holding the outer tube in position in the vaginal channel whilst the inner tube is being slid forward to eject the tampon from the outer tube into the body. Additionally or alternatively, a grip feature may be provided on the outer surface of the outer tube at its rear end. A grip feature may include, for example, a raised pattern or a different texture. A grip feature may extend completely around the external circumference of the outer tube. Alternatively, one or more discrete grip features may be provided. A plurality of discrete grip features may be provided, the grip features positioned substantially equidistantly around the external circumference of the outer tube. Two discrete grip features may be provided, the grip features being positioned substantially diametrically opposite to each other on the outer surface of the outer tube. Two discrete grip features on the outer surface of the outer tube may automatically lead the user to grip the outer tube with their thumb and index finger, which can provide an optimum and stable grip and can permit the applicator to function optimally.

The longitudinal length of the outer tube may vary around the circumference due to the rear end of the outer tube having a circumferential edge which is of a wave or undulating form. The outer tube may have a greater longitudinal length where discrete grip features are present and a smaller longitudinal length where discrete grip features are not present. This arrangement provides a larger grip area.

One or more protrusions may be provided on the outer surface of the forward end of the inner tube. The internal diameter of the outer tube at the location of the annular protrusion may be smaller than the external diameter of the inner tube including the protrusions provided thereon such that the protrusions on the outer surface of the inner tube are configured to engage with the annular protrusion on the inner surface of the outer tube to thereby prevent the inner tube from sliding completely out of the outer tube at the rear end of the outer tube.

A plurality of petals may be provided at the forward end of the inner tube. At least one protrusion may be provided on the outer surface of each petal. The protrusion may be provided at the base of the petal.

A plurality of petals may be provided at the forward end of the outer tube. Each petal may be provided, on its inner surface, with a spike. The spike may extend from the inner surface of the petal towards the forward end of the petal. The spike may engage with the forward end of the tampon to hold the tampon in position, relative to the outer tube, whilst the inner tube is slid rearwards relative to the outer tube. The tampon may then exit the inner tube via the front end of the inner tube and be positioned in the outer tube with the inner tube being positioned behind the tampon, ready to push the tampon forwards and out of the front end of the outer tube.

The spikes may be provided at the base of each petal on the inside surface of the outer tube.

It may be advantageous to provide a different number of spikes on the outer tube than protrusions on the inner tube and/or to arrange the spikes and protrusions at different intervals around the circumference of their respective tubes. This may help to prevent the spikes and protrusions from undesirably engaging each other and thereby making it difficult to slide the inner tube relative to the outer tube.

Each petal of the inner tube may have a single protrusion and each petal of the outer tube may have a single spike. More spikes may be provided on the outer tube in total than protrusions on the inner tube in total. The inner tube may have fewer petals than the outer tube. The inner tube may have an even number of petals and the outer tube may have an odd number of petals, or vice versa. The inner tube may have four petals and the outer tube may have five petals.

The inner tube and the outer tube may be formed from a thermoplastic material, such as a medical device classified thermoplastic material for example. The inner and outer tube may be formed from low density polyethylene (LDPE). The inner tube may be formed from a more rigid material or a stiffer material than the outer tube. For example, the outer tube may be formed from LDPE and the inner tube may be formed from polypropylene (PP). This permits the outer tube to be formed from a softer and/or more resilient material than the inner tube so that the outer tube is more comfortable when inserted into the body of a user. The inner tube may be formed of a more rigid or stiffer material to assist in pushing the tampon out from the outer tube of the applicator into the body of a user.

The applicator may further comprise a tampon disposed in the inner tube.

The applicator may consist of or comprise an inner tube and an outer tube and a tampon disposed in the inner tube.

BRIEF DESCRIPTION OF DRAWINGS

The present invention will now be described by way of example only and with reference to the following drawings, of which.

DETAILED DESCRIPTION OF PARTICULAR EMBODIMENTS

Figure 1:
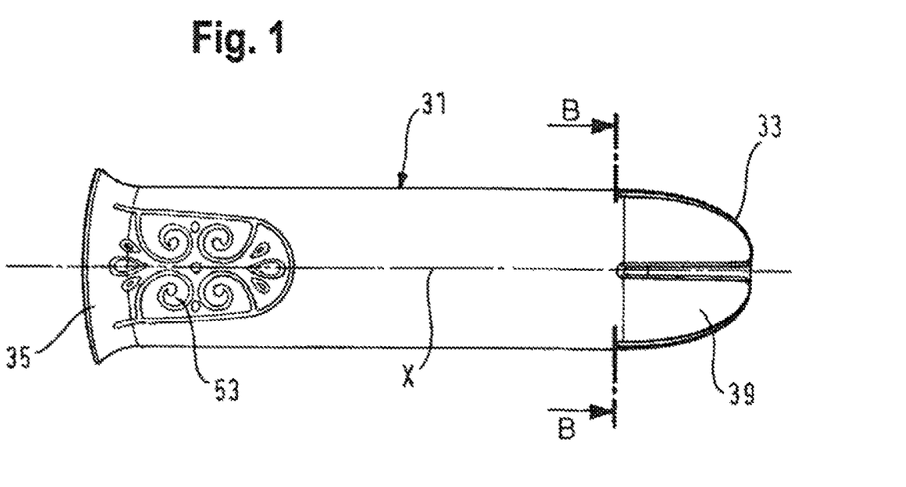
FIG. 1 shows a plan view of an outer tube of a tampon applicator in accordance with an embodiment of the invention.
Figure 2:
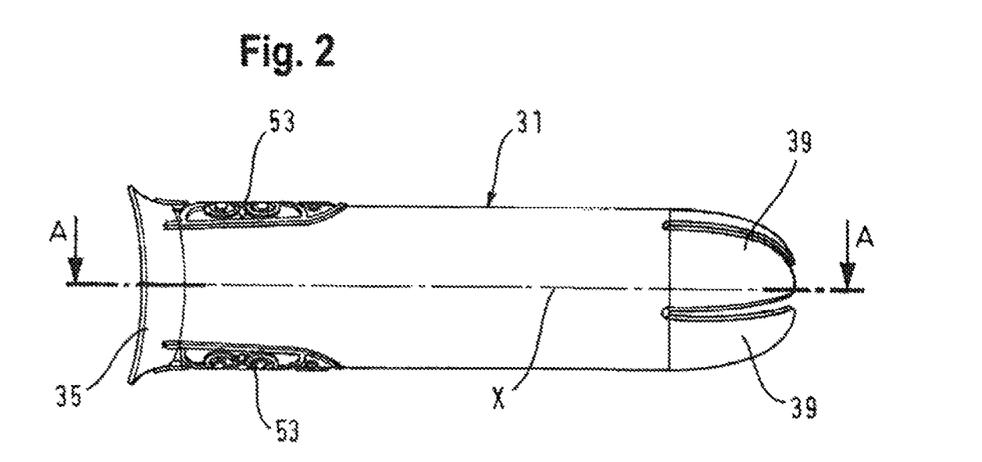
FIG. 2 shows a side view of the outer tube of FIG. 1.

An outer tube 31 of a tampon applicator is shown in FIGS. 1 and 2. The direction along the longitudinal axis of the outer tube is shown as X. The outer tube 31 has a front end 33 and a rear end 35. The front end 33 of the outer tube 31 includes a plurality of petals 39. In this depicted embodiment, five identical petals are provided, the petals being evenly spaced around the circumference of the outer tube. In other embodiments, the petals may not be identical, and/or may not be spaced evenly around the circumference of the inner tube. Fewer or more than five petals may be provided.

The external diameter of the outer tube 31 of FIG. 1 is tapered at its rearward end such that the external diameter of the outer tube increases towards the rear end 35 of the outer tube 31. In other embodiments, the external diameter of the outer tube may be not tapered.

In this depicted embodiment, a grip feature 53 is provided on the outer surface of the outer tube at its rear end. The grip feature may include, for example, a raised pattern or a different texture. In this depicted embodiment, there are two discrete grip features 53 provided which are positioned substantially diametrically opposite to each other on the outer surface of the outer tube. In other embodiments, a grip feature may extend around the external circumference of the outer tube.

In this embodiment, the longitudinal length of the outer tube 31 varies around the circumference due to the rear end 35 of the outer tube having a circumferential edge which is of a wave or undulating form. In this embodiment, the outer tube has a greater longitudinal length where the discrete grip features 53 are present and a smaller longitudinal length where the discrete grip features 53 are not present. In other embodiments, the outer tube 31 may be of a more regular form, having a longitudinal length which does not vary around the circumference.

Figure 3:
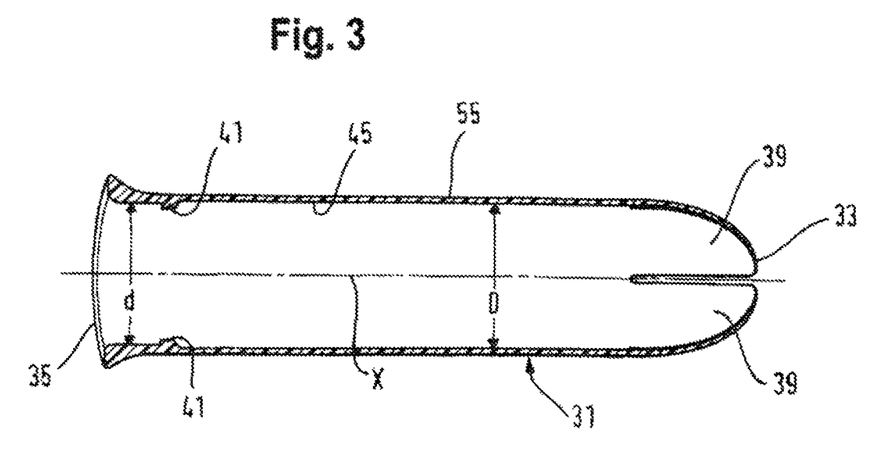
FIG. 3 shows a section through the outer tube of FIG. 1 along its longitudinal length.
Figure 4:
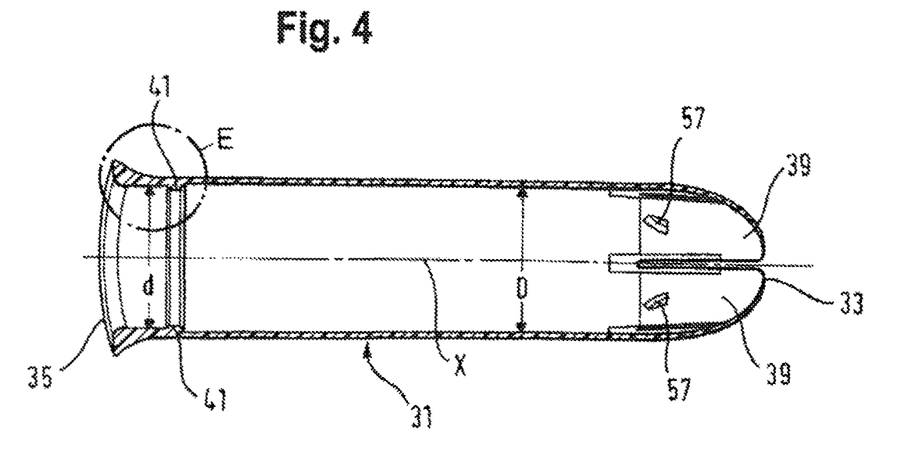
FIG. 4 shows the section A-A of the outer tube of FIG. 2.
Figure 5:
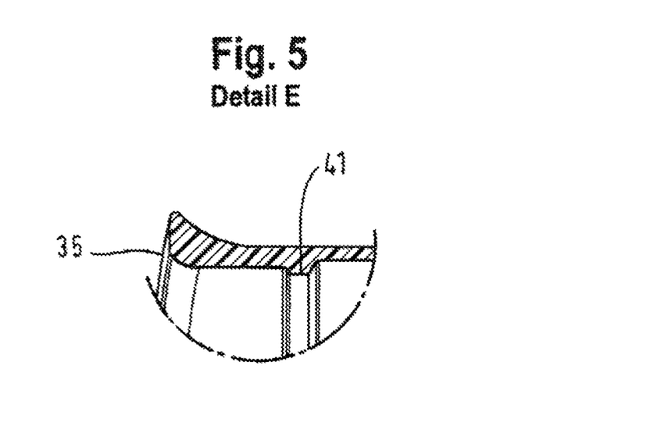
FIG. 5 shows a detail E of FIG. 4.

As can be seen in FIGS. 3-5, an annular ring, rim or protrusion 41 is provided within the outer tube 31 at or near to the rear end 35 of the outer tube 31. The annular protrusion 41 of the outer tube may extend radially inwardly substantially at a right angle from the interior surface 45 of the outer tube 31. The annular protrusion may be used, in conjunction with protrusions provided on the outer surface of the inner tube, to retain the inner tube in the outer tube by stopping the inner tube from sliding completely out of the outer tube when the inner tube is slid backwards relative to the outer tube.

Figure 7:
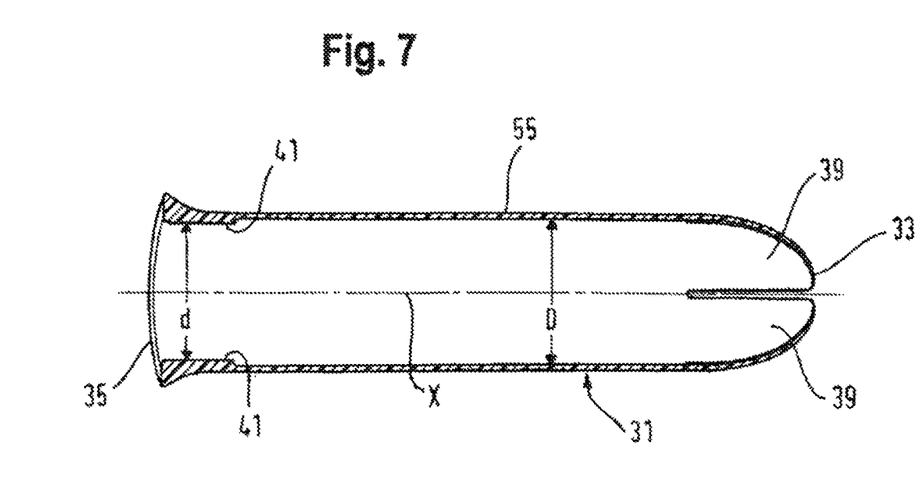
FIG. 7 shows a section through an outer tube along its longitudinal length in accordance with a further embodiment of the invention.

From FIG. 3 it can be seen that the main or central portion 55 of the outer tube 31 has an internal diameter D. The internal diameter of the outer tube 31 is smaller than D at the region of the annular protrusion 41. Rearward of the annular protrusion 41, the internal diameter of the outer tube 31 is d, where D>d. The internal diameter d may be larger than the internal diameter at the region of the annular protrusion 41 as shown in FIG. 3. Alternatively, the internal diameter d may be the same as or similar to the internal diameter at the region of the annular protrusion 41 as shown in FIG. 7.

FIG. 4 shows the section A-A of the outer tube 31. Part E of the rear end 35 of the outer tube 31 is shown in greater detail in FIG. 5. It can be seen from FIGS. 4 and 5 that D>d.

FIG. 4 also shows a spike 57 provided on the inner surface of each of the petals 39 of the outer tube 31. In some embodiments, the spike may extend from the inner surface of the petal 39 towards the forward end of the petal. The spike 57 is configured to engage with the forward end of the tampon to hold the tampon in position, relative to the outer tube 31, whilst the inner tube is slid rearwards relative to the outer tube.

In the depicted embodiment, a spike 57 is provided at the base of each petal 39 on the inside surface of the outer tube. In other embodiments, a spike may be provided on the inside surface of the outer tube rearward of the petals, or alternatively a spike may be provided in the middle of a petal or towards the front end of a petal. In the depicted embodiment, one spike 57 is provided on each petal. In other embodiments, more than one spike may be provided on a petal.

Figure 6:
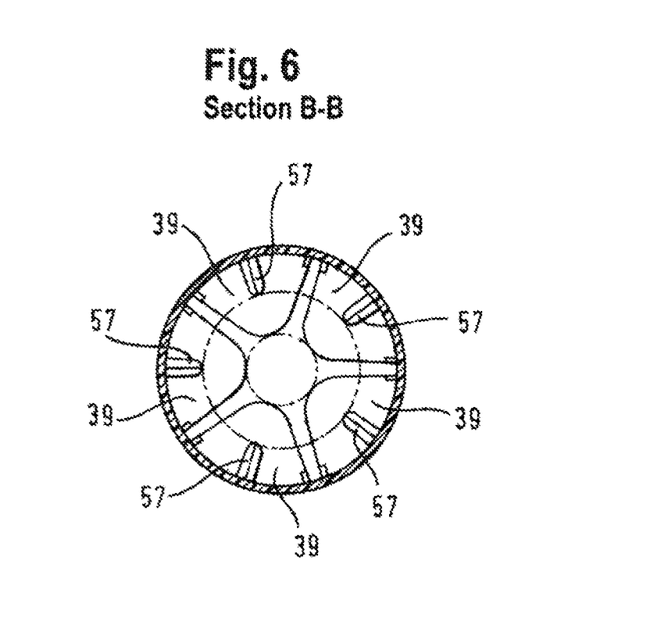
FIG. 6 shows the section B-B of the outer tube of FIG. 1.

FIG. 6 shows the section B-B of the outer tube. The petals 39 and the spikes 57 can also be seen in this figure.

Figure 8:
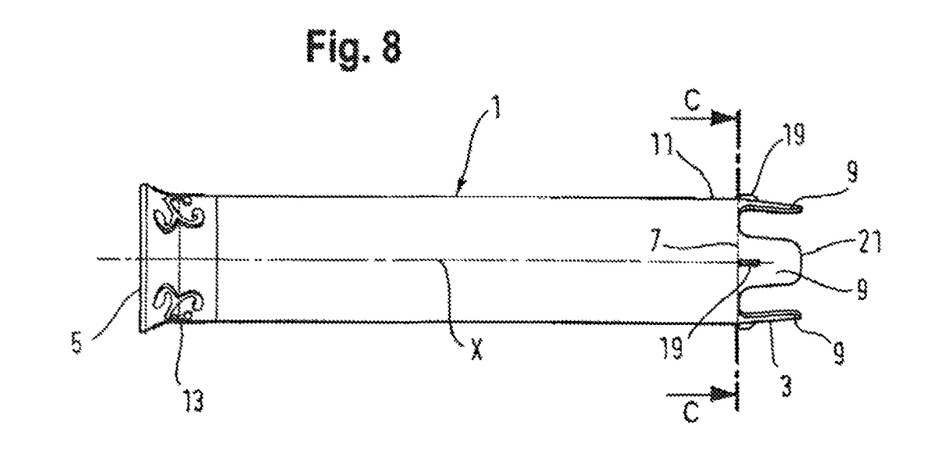
FIG. 8 shows a plan view of an inner tube in accordance with an embodiment of the invention.
Figure 9:
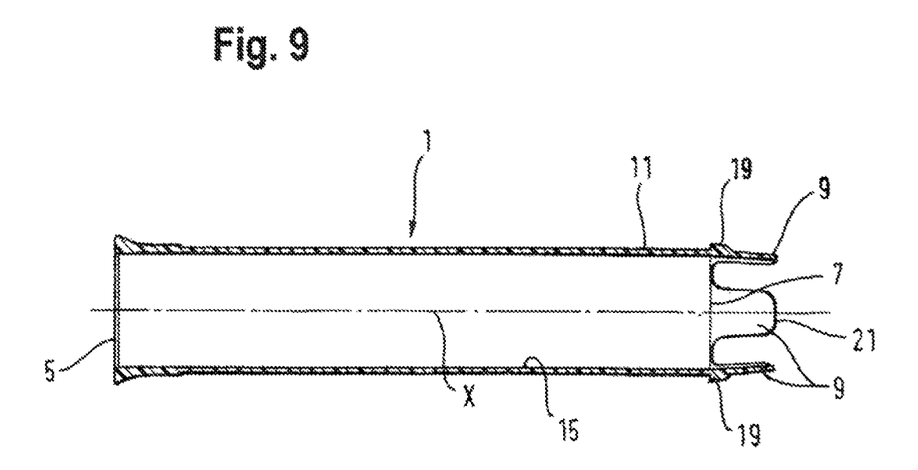
FIG. 9 shows a section through the inner tube of FIG. 8 along its longitudinal length.

FIGS. 8 and 9 show an inner tube 1 having a longitudinal axis X. The inner tube 1 has a front end 3 and a rear end 5. The front end 3 of the inner tube 1 includes a plurality of petals 9. In this depicted embodiment, four identical petals are provided, the petals being evenly spaced around the circumference of the inner tube. In other embodiments, the petals may not be identical, and/or may not be spaced evenly around the circumference of the inner tube. It is advantageous to provide at least two petals. In embodiments of the invention two, three, four, five, six or more petals may be provided.

In this depicted embodiment, a protrusion 19 is provided at the base 7 of each petal 9. In other embodiments, one or more protrusions may instead be provided rearward of the petals 9 on the outer surface 11 of the inner tube 1. In this depicted embodiment, a single protrusion 19 is provided at the base 7 of each petal 9. However, in other embodiments two or more protrusions may be provided at the base of each petal.

The protrusions extend in a radially outward direction from the outer surface 11 of the inner tube 1. In this embodiment, each protrusion 19 extends from the base 7 of a petal 9 in the longitudinal direction X of the inner tube towards the forward end 21 of the petal 9. The length of the protrusion 19 in the longitudinal direction X may be at least a quarter of the distance between the base 7 of the petal 9 and the forward end 21 of the petal 9, and may be a third or even a half of this distance.

The protrusions 19 cause the petals 9 to bend inwards so that the forward end 3 of the inner tube has a tapered shape in the region of the petals 9, as can be seen in FIGS. 8 and 9. A tapered inner tube front end 3 may be beneficial for engaging with the rear end of a tampon and in pushing the tampon out of an outer tube of an applicator.

The rear end 5 of the inner tube 1 may be tapered such that the rear end 5 of the inner tube 1 is wider than the remainder of the inner tube 1. This may assist in preventing the inner tube from being pushed entirely within an outer tube. The rear end 5 of the inner tube may include decorative or grip features 13 which may assist a user to firmly grip the rear end 5 of the inner tube 1 between their fingers, thereby facilitating use of the applicator.

Figure 10:
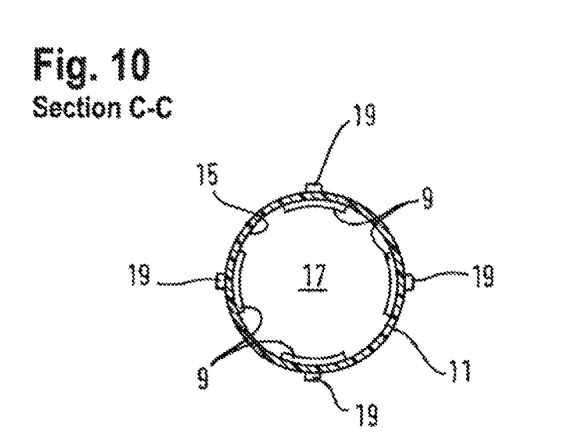
FIG. 10 shows the section C-C of the inner tube of FIG. 8.

FIG. 10 shows a cross-section through the inner tube at the position shown as C-C in FIG. 8. The inner tube 1 defines an interior space 17 for receiving a tampon. The inner tube 1 has an inner surface 15 and an outer surface 11. The protrusions 19 and petals 9 can be seen in FIG. 10.

Figure 11:
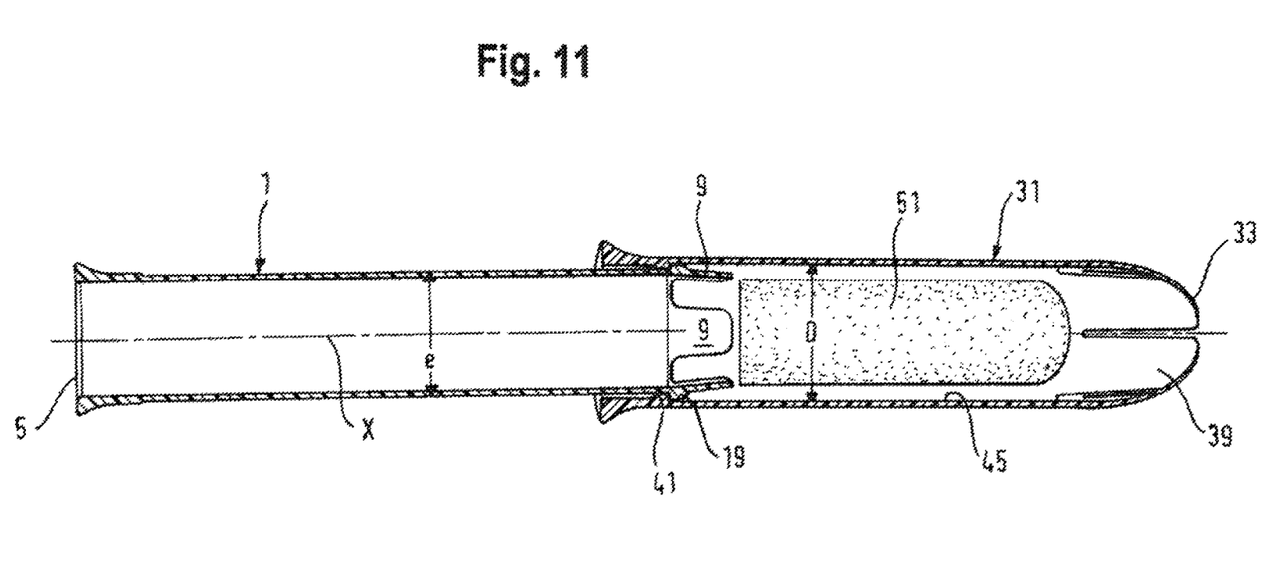
FIG. 11 shows a longitudinal cross-sectional view through a tampon applicator in accordance with an embodiment of the invention.

From FIG. 11 it can be seen that the internal diameter D of the outer tube 31 is slightly greater than the external diameter e of the inner tube 1, to enable the inner tube to slide within the outer tube. Initially, a tampon is at least partly located within the inner tube and the inner tube is almost entirely located within the outer tube, except for the rearmost part of the inner tube. To use the applicator, a user grips the rearmost part of the inner tube and slides the inner tube backwards relative to the outer tube. The spikes 57 provided on the inner surface of the petals 39 of the outer tube 31 (as shown in FIGS. 4 and 6) hold the tampon in position relative to the outer tube whilst the inner tube slides rearwardly relative to the outer tube. This allows the inner tube to slide rearwardly away from the tampon and to leave the tampon in the outer tube 31. The inner tube 1 is then positioned behind the tampon 51 as shown in FIG. 11.

The internal diameter of the outer tube 31 at the region of the annular protrusion 41 is smaller than the external diameter of the protrusions 19 (i.e. the external diameter of the inner tube at the location of the protrusions 19), such that the protrusions 19 of the inner tube engage the annular protrusion 41 of the outer tube to prevent the inner tube from sliding backwards completely out of the outer tube.

Once the inner tube 1 has been slid backwards with respect to the outer tube 31 to the position shown in FIG. 11, the outer tube 31 is inserted into the body of a user and the user gently pushes the inner tube 1 in a forwards direction into the outer tube 31. This causes the petals 9 of the inner tube 1 to contact the tampon 51 and to push the tampon 51 into the body of the user. As previously explained, if the longitudinal axis X of the inner tube and the longitudinal axis X of the outer tube are not aligned, the inner tube 1 makes contact with the inner surface 45 of the outer tube 31 resulting in the user having to apply more force to the inner tube 1 in order to push the inner tube into the outer tube to expel the tampon from the outer tube 31. It is desirable to reduce the force required to expel the tampon from the outer tube, and this may be achieved by ensuring that the longitudinal axis X of the inner and outer tubes remain in alignment whilst the inner tube is being pushed back into the outer tube. However, when a user pushes the inner tube back into the outer tube from its extended position, the longitudinal axis of the inner tube often does not align with the longitudinal axis of the outer tube. The user may not be able to accurately judge whether the inner and outer tubes are aligned or not and may simply push the inner tube forwards.

By providing the outer tube with a smaller internal diameter d rearward of the annular protrusion 41, the inner tube 1 has less freedom of movement in directions other than the direction of the longitudinal axis X of the outer tube, with the result that the longitudinal axis X of the inner tube is more closely aligned with the longitudinal axis X of the outer tube as the inner tube is slid into the outer tube.

While the foregoing description and drawings represent exemplary embodiments of the present invention, it will be understood that various additions, modifications and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

The invention claimed is:

1. An applicator for a tampon, comprising:
    an inner tube and an outer tube, the inner tube being slideable within the outer tube and including a tampon disposed in the inner tube, the applicator having a forward end, wherein an inner surface of the outer tube comprises an annular protrusion near to a rear end of the outer tube having at least one surface which extends radially inwardly substantially at a right angle from the inner surface of the outer tube and an internal diameter of the outer tube is smaller rearward of the annular protrusion than forward of the annular protrusion, and wherein the rear end of the outer tube has a circumferential edge which is a wave form;
    a grip feature arranged adjacent to a rear end of the outer tube, the grip feature including discrete grip features positioned opposite to each other on the outer surface of the outer tube, and wherein
    the grip features are positioned relative to the wave form of the rear end such that the outer tube has a greater longitudinal length where the discrete grip features are present and a smaller longitudinal length where the discrete grip features are not present, the longitudinal length of the outer tube varying due to the wave form,
    wherein petals are provided at a forward end of the inner tube and a protrusion is provided at a base of each petal where the petal bends, such that each protrusion is engageable with the annular protrusion to prevent the inner tube from sliding completely out of the outer tube at the rear end.

2. The applicator for a tampon according to claim 1 wherein the internal diameter of the outer tube rearward of the annular protrusion is greater than the internal diameter of the outer tube at a region of the annular protrusion.

3. The applicator for a tampon according to claim 1 wherein the internal diameter of the outer tube rearward of the annular protrusion is substantially constant along the longitudinal length of the outer tube from the annular protrusion to the rear end of the outer tube.

4. The applicator for a tampon according to claim 1 wherein the internal diameter of the outer tube rearward of the annular protrusion is tapered along the longitudinal length of the outer tube from the annular protrusion to the rear end of the outer tube, the internal diameter of the outer tube rearward of the annular protrusion being smaller throughout the taper than the internal diameter of the outer tube forward of the annular protrusion.

5. The applicator for a tampon according to claim 1 wherein an external diameter of the outer tube is tapered at the rear end of the outer tube such that the external diameter of the outer tube increases towards the rear end of the outer tube.

6. The applicator for a tampon according to claim 1 wherein an internal diameter of the outer tube at the location of the annular protrusion is smaller than an external diameter of the inner tube including each of the protrusions such that the protrusions engage with the annular protrusion on the inner surface of the outer tube to prevent the inner tube from sliding completely out of the outer tube at the rear end.

7. The applicator for a tampon according to claim 1 wherein the outer tube comprises a plurality of petals at a forward end of the outer tube and each petal is provided, on an inner surface of each petal at a base of the petal, with a spike which extends from an inner surface of the petal towards the forward end of the outer tube.

8. The applicator for a tampon according to claim 7, wherein a single protrusion is provided for each petal of the inner tube, and wherein a single spike is provided on each petal of the outer tube, and wherein a number of protrusions at the forward end of the inner tube is not the same as a number of spikes at the forward end of the outer tube.

9. The applicator for a tampon according to claim 8 wherein the number of spikes at the forward end of the outer tube is greater than the number of protrusions at the forward end of the inner tube.

10. An applicator for a tampon, comprising:
    an outer tube having a forward end and a rear end opposite the forward end;

an inner tube slideable within the outer tube, wherein an inner surface of the outer tube comprises an annular protrusion near to the rear end having at least one surface which extends radially inwardly substantially at a right angle from the inner surface and an internal diameter of the outer tube is smaller rearward of the annular protrusion than forward of the annular protrusion;

petals at a forward end of the inner tube, each petal having a base at which the corresponding petal bends; and a protrusion at the base of each petal, the protrusion causing a corresponding petal to bend inwardly, wherein the internal diameter of the outer tube at the annular protrusion is smaller than an external diameter of the inner tube including each protrusion such that each protrusion engages with the annular protrusion to prevent the inner tube from sliding completely out of the outer tube.

* * * * *